(12) United States Patent
Shi et al.

(10) Patent No.: US 8,729,224 B2
(45) Date of Patent: *May 20, 2014

(54) MELANOCORTIN RECEPTOR-SPECIFIC PEPTIDES FOR TREATMENT OF FEMALE SEXUAL DYSFUNCTION

(71) Applicant: Palatin Technologies, Inc., Cranbury, NJ (US)

(72) Inventors: Yi-Qun Shi, East Brunswick, NJ (US); Shubh D. Sharma, Cranbury, NJ (US); Wei Yang, Edison, NJ (US); Xin Chen, Furlong, PA (US)

(73) Assignee: Palatin Technologies, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/910,506

(22) Filed: Jun. 5, 2013

(65) Prior Publication Data

US 2013/0288987 A1  Oct. 31, 2013

Related U.S. Application Data

(63) Continuation of application No. 12/952,238, filed on Nov. 23, 2010, now Pat. No. 8,487,073, which is a continuation of application No. PCT/US2009/046571, filed on Jun. 8, 2009.

(60) Provisional application No. 61/059,910, filed on Jun. 9, 2008.

(51) Int. Cl.
*A61K 38/12* (2006.01)

(52) U.S. Cl.
USPC ............ 530/317; 530/323; 514/3.6; 514/10.7

(58) Field of Classification Search
None
See application file for complete search history.

(56) References Cited

U.S. PATENT DOCUMENTS

| | | |
|---|---|---|
| 5,576,290 A | 11/1996 | Hadley |
| 5,674,839 A | 10/1997 | Hruby et al. |
| 5,731,408 A | 3/1998 | Hadley et al. |
| 6,054,556 A | 4/2000 | Huby et al. |
| 6,350,430 B1 | 2/2002 | Dooley et al. |
| 6,476,187 B1 | 11/2002 | Cone et al. |
| 6,579,968 B1 | 6/2003 | Blood et al. |
| 6,600,015 B2 | 7/2003 | Chen et al. |
| 6,613,874 B1 | 9/2003 | Mazur et al. |
| 6,693,165 B2 | 2/2004 | Bednarek |
| 6,699,873 B1 | 3/2004 | Maguire et al. |
| 6,794,489 B2 | 9/2004 | Blood et al. |
| 6,887,846 B2 | 5/2005 | Catania et al. |
| 6,951,916 B2 | 10/2005 | Mazur et al. |
| 7,008,925 B1 | 3/2006 | Szardenings et al. |
| 7,176,279 B2 | 2/2007 | Sharma et al. |
| 7,541,430 B2 | 6/2009 | Sensfuss et al. |
| 8,487,073 B2 * | 7/2013 | Shi et al. .................. 530/317 |
| 2001/0056179 A1 | 12/2001 | Chen et al. |
| 2002/0143141 A1 | 10/2002 | Chen et al. |
| 2003/0064921 A1 | 4/2003 | Millhauser et al. |

(Continued)

FOREIGN PATENT DOCUMENTS

| | | |
|---|---|---|
| CA | 1340107 | 10/1998 |
| CA | 2158425 C | 1/2003 |

(Continued)

OTHER PUBLICATIONS

Oosterom, J., et al., "Common Requirements for Melanocortin-4 Receptor Selectivity of Structurally Unrelated Melanocortin Agonist and Endogenous Antagonist, Agouti Protein", The Journal of Biological Chemistry, 2001, 276: 931-936.

Ballet, S., et al., "Novel selective human melanocortin-3 receptor ligands: Use of the 4-amino-1,2,4,5-tetrahydro-2-benzazepin-3-one (Aba) scaffold", Bioorg. Med. Chem. Lett., May 1, 2007; 17(9): 2492-2498.

Vrinten, D., et al., "Antagonism of the Melanocortin System Reduces Cold and Mechanical Allodynia in Mononeuropathic Rats", The Journal of Neuroscience, Nov. 1, 2000, 20(21):8131-8137.

(Continued)

*Primary Examiner* — James H Alstrum Acevedo
*Assistant Examiner* — Jeanette Lieb
(74) *Attorney, Agent, or Firm* — Stephen A. Slusher

(57) ABSTRACT

Methods for use of a melanocortin receptor agonist cyclic peptide of the formula where R, x and y are as defined in the specification, and compositions and formulations including the peptide of the foregoing formula, for preventing, ameliorating or treating female sexual dysfunction.

9 Claims, 1 Drawing Sheet

(56) References Cited

U.S. PATENT DOCUMENTS

| | | |
|---|---|---|
| 2003/0105024 A1 | 6/2003 | Cone et al. |
| 2003/0113263 A1 | 6/2003 | Marks et al. |
| 2003/0212002 A1 | 11/2003 | Haskell-Luevano et al. |
| 2004/0023859 A1 | 2/2004 | Mazur et al. |
| 2004/0138136 A1 | 7/2004 | Sharma et al. |
| 2005/0038230 A1 | 2/2005 | Sharma et al. |
| 2005/0075344 A1* | 4/2005 | Backer et al. ............ 514/252.13 |
| 2005/0101535 A1 | 5/2005 | Rosenstein et al. |
| 2005/0130901 A1 | 6/2005 | Lipton et al. |
| 2005/0164914 A1 | 7/2005 | Sharma et al. |
| 2005/0187164 A1 | 8/2005 | Pinel |
| 2005/0222014 A1 | 10/2005 | Diamond et al. |
| 2005/0239711 A1 | 10/2005 | Chen et al. |
| 2006/0014194 A1 | 1/2006 | Sharma et al. |
| 2006/0041021 A1 | 2/2006 | Wilson et al. |
| 2006/0105951 A1 | 5/2006 | Cunningham et al. |
| 2006/0111281 A1 | 5/2006 | Sharma et al. |
| 2006/0135436 A1 | 6/2006 | Haskell-Luevano et al. |
| 2006/0258590 A1 | 11/2006 | Haskell-Luevano |
| 2006/0293223 A1 | 12/2006 | Gadski et al. |
| 2007/0027091 A1* | 2/2007 | Conde-Frieboes et al. ..... 514/16 |
| 2007/0105759 A1 | 5/2007 | Flora et al. |
| 2007/0123453 A1 | 5/2007 | Heiman et al. |
| 2007/0244054 A1 | 10/2007 | Sensfuss et al. |
| 2007/0293423 A1 | 12/2007 | Jungheim et al. |
| 2008/0039387 A1 | 2/2008 | Sensfuss et al. |
| 2009/0305960 A1 | 12/2009 | Chen et al. |
| 2010/0311648 A1 | 12/2010 | Dodd et al. |

FOREIGN PATENT DOCUMENTS

| | | |
|---|---|---|
| CN | 1563076 A | 1/2005 |
| CN | 1709906 A | 12/2005 |
| WO | 92/00995 A1 | 1/1992 |
| WO | 94/22460 A1 | 10/1994 |
| WO | 97/40070 A1 | 10/1997 |
| WO | 98/10068 A2 | 3/1998 |
| WO | 98/27113 A2 | 6/1998 |
| WO | 99/21571 A1 | 5/1999 |
| WO | 99/54358 A1 | 10/1999 |
| WO | 00/01730 A1 | 1/2000 |
| WO | 00/05263 A2 | 2/2000 |
| WO | 00/35952 A2 | 6/2000 |
| WO | 00/58361 A1 | 10/2000 |
| WO | 01/00224 A1 | 1/2001 |
| WO | 01/30808 A1 | 5/2001 |
| WO | 01/52880 A1 | 7/2001 |
| WO | 01/74844 A2 | 10/2001 |
| WO | 01/85930 A2 | 11/2001 |
| WO | 01/90140 A1 | 11/2001 |
| WO | 02/18437 A2 | 3/2002 |
| WO | 02/26774 A2 | 4/2002 |
| WO | 02/094873 A2 | 11/2002 |
| WO | 03/006604 A2 | 1/2003 |
| WO | 03/006620 A3 | 1/2003 |
| WO | 2006/032457 A1 | 3/2003 |
| WO | 03/095474 A2 | 11/2003 |
| WO | 2004/005324 A2 | 1/2004 |
| WO | 2004/046166 A2 | 6/2004 |
| WO | 2004/099246 A2 | 11/2004 |
| WO | 2005/000338 A1 | 1/2005 |
| WO | 2005/000339 A2 | 1/2005 |
| WO | 2005/000877 A2 | 1/2005 |
| WO | 2005/014617 A2 | 2/2005 |
| WO | 2005/030797 A2 | 4/2005 |
| WO | 2005/048967 A1 | 6/2005 |
| WO | 2005/060985 A1 | 7/2005 |
| WO | 2005/102377 A1 | 11/2005 |
| WO | 2006/012667 A1 | 2/2006 |
| WO | 2006/014552 A2 | 2/2006 |
| WO | 2006/037188 A1 | 4/2006 |
| WO | 2006/048449 A2 | 5/2006 |
| WO | 2006/048450 A2 | 5/2006 |
| WO | 2006/048451 A1 | 5/2006 |
| WO | 2006/048452 A2 | 5/2006 |
| WO | 2006/060873 A1 | 6/2006 |
| WO | 2006/073771 A2 | 7/2006 |
| WO | 2006/076442 A2 | 7/2006 |
| WO | 2006/097526 A1 | 9/2006 |
| WO | 2006/129317 A1 | 12/2006 |
| WO | 2007/008684 A2 | 1/2007 |
| WO | 2007/008704 A2 | 1/2007 |
| WO | 2007/009894 A2 | 1/2007 |
| WO | 2007/027574 A2 | 3/2007 |
| WO | 2007/035474 A2 | 3/2007 |
| WO | 2008/056207 A1 | 5/2008 |
| WO | 2008/087186 A2 | 7/2008 |
| WO | 2008/087187 A1 | 7/2008 |
| WO | 2008/087188 A2 | 7/2008 |
| WO | 2008/087189 A2 | 7/2008 |
| WO | 2008/087190 A2 | 7/2008 |
| WO | 2008/142319 A2 | 11/2008 |
| WO | 2008/156677 A2 | 12/2008 |
| WO | 2009/151383 A1 | 12/2009 |
| WO | 2009/152079 A1 | 12/2009 |
| WO | 2010/144341 A2 | 12/2010 |
| WO | 2010/144341 A3 | 12/2010 |

OTHER PUBLICATIONS

Hruby, V., et al., "Cyclic Lactam α-Melanotropin Analogues of Ac-Nle4-cyclo[Asp5,D-Phe7,Lys10] α-Melanocyte-Stimulating Hormone-(4-10)-NH2 with Bulky Aromatic Amino Acids at Position 7 Show High Antagonist Potency and Selectivity at Specific Melanocortin Receptors", J. Med. Chem., 1995, 38: 3454-3461.

Maaser, C., et al., "Role of the Melanocortin System in Inflammation", Ann. N.Y. Acad. Sci., 2006, 1072: 123-134.

Giuliani, D., et al., "Selective melanocortin MC4 Receptor agonists reverse haemorrhagic shock and prevent multiple organ damage", Research Paper, British Journal of Pharmacology, 2007, 150: 595-603.

Bednarek, M., et al., "Analogs of Lactam Derivatives of α-Melanotropin with Basic and Acidic Residues", Biochemical and Biophysical Research Communications, 2000, 272: 23-28.

Yan, L.Z., et al., "Structure-Activity Relationships of β-MSH Derived Melanocortin-4 Receptor Peptide Agonists", Current Topics in Medicinal Chemistry, 2007, 7:052-1067.

Grieco, P., et al., "Structure-activity studies of new melanocortin peptides containing an aromatic amino acid at the N-terminal position", Peptides 2006, 27: 472-481.

Gautron, L., et al., "Melanocortin-4 Receptor Expression in a Vagovagal Circuitry Involved in Postprandial Functions", Research Article, The Journal of Comparative Neurology, 2010, 518:6-24.

Navarro, M., et al., "Effects of Melanocortin Receptor Activation and Blockade on Ethanol Intake: A Possible Role for the Melanocortin-4 Receptor", Alcohol Clin. Exp. Res., Jun. 2005, 29(6): 949-957.

Adan, Rah, et al., "The MC4 receptor and control of appetite", British Journal of Pharmacology, 2006, 149: 815-827.

Adan et al., "Characterization of melanocortin receptor ligands on cloned brain melanocortin receptors and on grooming behavior in the rat," European Journal of Pharmacology, 1999, 378: 249-258.

Bednarek et al., "Analogs of MTII, Lactam Derivatives of a-Melanotropin, Modified at the N Terminus, and Their Selectivity at Human Melanocortin Receptors 3, 4, and 5," Biochemical and Biophysical Research Communications, 1999, 261: 209-213.

Bednarek et al., "Cyclic analogs of alpha-melanocyte-stimulating hormone (alphaMSH) with high agonist potency and selectivity at human melanocortin receptor 1b," Peptides, 2008, 29(6): 1010-1017.

Schaaper et al., "Synthesis of cyclic alpha-MSH peptides," Letters in Peptide Science, 1998, 5(2-3): 205-208.

Todorovic et al., "A review of melanocortin receptor small molecule ligands," Peptides, 2005, 26(10): 2026-2036.

Wikberg et al., "Targeting melanocortin receptors: an approach to treat weight disorders and sexual dysfunction," Nat. Rev. Drug Discov., 2008, 7(4): 307-323.

International Search Report by U.S. Patent Office in PCT/US 09/46571 with mailing date of Nov. 3, 2009.

(56) References Cited

OTHER PUBLICATIONS

Written Opinion of the International Searching Authority (U.S. Patent Office) in PCT/US 09/46571 with mailing date of Nov. 3, 2009.
International Search Report by U.S. Patent Office in PCT/US2010/037589, published as WO 2010/144344 A3 on Dec. 16, 2010.
Written Opinion of the International Searching Authority (U.S. Patent Office) in PCT/US 10/37589 with mailing date of Oct. 14, 2010.
Supplementary European Search Report by European Patent Office in EP 09 76 3370 with mailing date of Dec. 19, 2011.
Balbani, "Recent developments for smoking cessation and treatment of nicotine dependence," Expert Opin. Ther. Patents, 2007, 17(3): 287-297.
Balse-Srinivasa et al., "Structure-activity relationships of gamma-MSH analogues at the human melanocortin MC3, MC4, and MC5 receptors. Discovery of highly selective hMC3R, hMC4R, and hMC5R analogues," J. Med. Chem., 2003, 46(23): 4965-4973.
Bednarek et al., "Ligands of the melanocortin receptors, 2002-2003 update," Expert Opin. Ther. Patents, 2004, 14(3): 327-336.
Chan et al., "Molecular modelling of beta turns in a cyclic melanotropin," J. Pharm. Pharmacal., 1996, 48(2): 218-222.
Hadley, "The Proopiomelanocortin System," Annals New York Academy of Science, 1999, 885: 1-21.
Hruby et al., "A highly potent cyclic a-MSH antagonist containing naphthylalanine," Peptides: Chemistry, Structure and Biology, Proceedings of the American Peptide Symposium, 14th, Columbus, Ohio, Jun. 18-23, 1996, 364-365.
Hruby et al., "Design of potent and specific melanotropin agonists and antagonists: investigating ligands for new receptors," Peptides, 1996, Proceedings of the European Peptide Symposium, 24th, Edinburgh, Sep. 8-13, 1996 (1998), 485-486.
Nigenhuis et al., "Accelerating sensory recovery after sciatic nerve crush: non-selective versus melanocortin MC4 receptor-selective peptides," European Journal of Pharmacology, 2004, 495:145-152.
Nigenhuis et al., "Discovery and in vivo evaluation of new melanocortin-4 receptor-selective peptides," Peptides, 2003, 24:271-280.
Nogueiras et al., "The central melanocortin system directly controls peripheral lipid metabolism," J. Clin. Invest., 2007, 117(11): 3475-3488.
Nozawa et al., "Recent advances in the development of melanocortin-4 receptor ligands," Expert Opin. Ther. Patents, 2008, 18(4): 403-427.
Ujjainwalla et al., "Small molecule ligands of the human melanocortin-4 receptor," Curr. Top. Med. Chem., 2007, 7(11): 1068-1084.
R. Jordan, et al., Developing Treatments for Female Sexual Dysfunction, Clinical Pharmacology & Therapeutics, V. 89, No. 1, Jan. 2011, pp. 137-141.
A. Shadiack, et al., Melanocortins in the Treatment of Male and Female Sexual Dysfunction, V. 7, 2007, pp. 1137-1144.
L. Diamond, et al., An Effect on the Subjective Sexual Response in Premenopausal Women . . . , J. Sex. Med., 2006, pp. 628-638.
J. Pfaus, et al., Bremelanotide: An Overview of Preclinical CNS Effects on Female Sexual Function, J. Sex. Med., 2007;4(suppl 4), pp. 269-279.
J. Pfaus, et al., Selective facilitation of sexual solicitation in the female rat by a melanocortin receptor agonist, PNAS, 2004, V.101,N. 27, pp. 10201-10204.
Michael A. Perelman, Clinical Application of CNS-Acting Agents in FSD, J. Sex. Med. 2007;4(suppl.4), pp. 280-290.
Mohammad Reza Safarinejad, Evaluation of the Safety and Efficacy of Bremelanotide, a Melanocortin Receptor Agonist, . . . , J. Sex. Med, 2007, pp. 1-11.

\* cited by examiner

SEQUENCE LISTING

```
<160> NUMBER OF SEQ ID NOS: 9

<210> SEQ ID NO 1
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (2)..(7)
<223> OTHER INFORMATION: cyclic peptide lactam bond
```

```
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 1

Xaa Asp His Xaa Arg Trp Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (2)..(7)
<223> OTHER INFORMATION: cyclic peptide lactam bond
<220> FEATURE:
<221> NAME/KEY: MISC_FEATURE
<222> LOCATION: (4)..(4)
<223> OTHER INFORMATION: D-Phe

<400> SEQUENCE: 2

Xaa Asp His Xaa Arg Trp Lys
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic melanocortin receptor binding core
      sequence derived from alpha-MSH

<400> SEQUENCE: 3

His Phe Arg Trp
1

<210> SEQ ID NO 4
<211> LENGTH: 7
<212> TYPE: PRT
<213> ORGANISM: Artificial Sequence
<220> FEATURE:
<223> OTHER INFORMATION: Synthetic melanocortin receptor binding peptide
      of the invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclic peptide lactam bond
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
```

```
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 4

Arg Asp Xaa Xaa Arg Trp Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic melanocortin receptor binding peptide
      of the invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclic peptide lactam bond
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe

<400> SEQUENCE: 5

Arg Asp Xaa Xaa Arg Trp Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic melanocortin receptor binding peptide
      of the invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclic peptide lactam bond
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 6

Arg Glu Xaa Xaa Arg Trp Xaa
1               5
```

```
<210> SEQ ID NO 7
<211> LENGTH: 7
<212> TYPE: PRT
<213> ORGANISM: Artificial Sequence
<220> FEATURE:
<223> OTHER INFORMATION: Synthetic melanocortin receptor binding peptide
      of the invention
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclic peptide lactam bond
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: Orn

<400> SEQUENCE: 7

Arg Glu Xaa Xaa Arg Trp Xaa
1               5

<210> SEQ ID NO 8
<211> LENGTH: 13
<212> TYPE: PRT
<213> ORGANISM: Artificial Sequence
<220> FEATURE:
<223> OTHER INFORMATION: Synthetic melanocortin binding sequence derived
      from human alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 8

Ser Tyr Ser Met Glu His Phe Arg Trp Gly Lys Pro Val
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic melanocortin binding sequence derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MISC_FEATURE
<222> LOCATION: (7)..(7)
<223> OTHER INFORMATION: D-Phe
<220> FEATURE:
<221> NAME/KEY: MOD_RES
<222> LOCATION: (13)..(13)
<223> OTHER INFORMATION: AMIDATION
```

```
<400> SEQUENCE: 9

Ser Tyr Ser Xaa Glu His Xaa Arg Trp Gly Lys Pro Val
1               5               10
```

MELANOCORTIN RECEPTOR-SPECIFIC PEPTIDES FOR TREATMENT OF FEMALE SEXUAL DYSFUNCTION

CROSS-REFERENCE TO RELATED APPLICATIONS

This application is a continuation application of U.S. Ser. No. 12/952,238, entitled "Melanocortin Receptor-Specific Peptides for Treatment of Sexual Dysfunction," filed on Nov. 23, 2010, now U.S. Pat. No. 8,487,073, issued on Jul. 16, 2013. U.S. Ser. No. 12/952,238 is a continuation of International Application No. PCT/US09/46571, published as International Publication No. WO 2009/152079, entitled "Melanocortin Receptor-Specific Peptides for Treatment of Sexual Dysfunction", filed on Jun. 8, 2009, which in turn claims priority to and the benefit of the filing of U.S. Provisional Patent Application Ser. No. 61/059,910 entitled "Melanocortin Receptor-Specific Peptides for Treatment of Sexual Dysfunction", filed on Jun. 9, 2008. The specification and claims of each of the foregoing are incorporated herein by reference.

BACKGROUND OF THE INVENTION

1. Field of the Invention (Technical Field)

The present invention relates to melanocortin receptor-specific cyclic peptides which may be used in the treatment of melanocortin receptor-mediated diseases, indications, conditions and syndromes.

2. Description of Related Art

The following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, midbrain and brainstem, and melanocortin-5 receptors (MC5-R), expressed in a wide distribution of peripheral tissues.

Significant work has been done in determining the structure of melanocortin receptors, including both the nucleic acid sequences encoding for the receptors and the amino acid sequences constituting the receptors. MC4-R is a G protein-coupled, 7-transmembrane receptor that is believed to be expressed primarily in the brain.

Peptides specific for MC4-R, and secondarily peptides specific for MC3-R, are believed to be useful in regulation of mammalian energy homeostasis, including use as agents for attenuating food intake and body weight gain. MC4-R agonist peptides are believed to be useful for treating sexual dysfunction, including male erectile dysfunction, and for decreasing food intake and body weight gain, such as for treatment of obesity. MC4-R agonist peptides may also be employed for decreasing voluntary ethanol consumption, treatment of drug addictions, and the like. Such peptides, as well as MC1-R and MC3-R agonist peptides, may further be employed for treatment of circulatory shock, ischemia, hemorrhagic shock, inflammatory diseases and related diseases, indications, conditions and syndromes. MC4-R antagonist peptides, by contrast, are believed to be useful for weight gain aid, such as for use in treatment of cachexia, sarcopenia, wasting syndrome or disease, and anorexia. Such peptides may also be employed for treatment of depression and related disorders.

Melanocortin receptor-specific peptides include cyclic α-melanocyte-stimulating hormone ("α-MSH") analog peptides such as Ac-Nle-cyclo(-Asp-His-D-Phe-Arg-Trp-Lys)-NH$_2$ (SEQ ID NO:1) (See U.S. Pat. Nos. 5,674,839 and 5,576,290) and Ac-Nle-cyclo(-Asp-His-D-Phe-Arg-Trp-Lys)-OH (SEQ ID NO:2) (See U.S. Pat. Nos. 6,579,968 and 6,794,489). These and other melanocortin receptor-specific peptides generally contain the central tetrapeptide sequence of native α-MSH, His$^6$-Phe$^7$-Arg$^8$-Trp$^9$ (SEQ ID NO:3), or a mimetic or variation thereof, including the substitution of D-Phe for Phe$^7$. Other peptides or peptide-like compounds asserted to be specific for one or more melanocortin receptors are disclosed in U.S. Pat. Nos. 5,731,408, 6,054,556, 6,350,430, 6,476,187, 6,600,015, 6,613,874, 6,693,165, 6,699,873, 6,887,846, 6,951,916, 7,008,925, and 7,176,279; in U.S. published patent application Publication Nos. 2001/0056179, 2002/0143141, 2003/0064921, 2003/0105024, 2003/0212002, 2004/0023859, 2005/0130901, 2005/0187164, 2005/0239711, 2006/0105951, 2006/0111281, 2006/0293223, 2007/0027091, 2007/0105759, 2007/0123453, 2007/0244054, and 2008/0039387; and in international patent applications nos. WO 98/27113, WO 99/21571, WO 00/05263, WO 99/54358, WO 00/35952, WO 00/58361, WO 01/30808, WO 01/52880, WO 01/74844, WO 01/85930, WO 01/90140, WO 02/18437, WO 02/26774, WO 03/006604, WO 2004/046166, WO 2005/000338, WO 2005/000339, WO 2005/000877, WO 2005/030797, WO 2005/060985, WO2006/048449, WO 2006/048450, WO 2006/048451, WO 2006/048452, WO 2006/097526, WO 2007/008684, WO 2007/008704, and WO 2007/009894.

Notwithstanding the intense scientific and pharmaceutical interest in melanocortin receptor-specific peptides, evidenced by numerous articles in the scientific literature and numerous patent applications and issued patents, no melanocortin receptor-specific peptide has been approved as a drug for any therapeutic indication. Indeed, there are no reports of any melanocortin receptor-specific peptide for any therapeutic indication having advanced past Phase II clinical trials. There remains a significant and substantial need for melanocortin receptor-specific peptides for use in pharmaceutical applications, and in particular for treatment of sexual dysfunction. It is against this background that the present invention was made.

BRIEF SUMMARY OF THE INVENTION

In one aspect, the present invention relates to a cyclic peptide of formula (I):

(I)

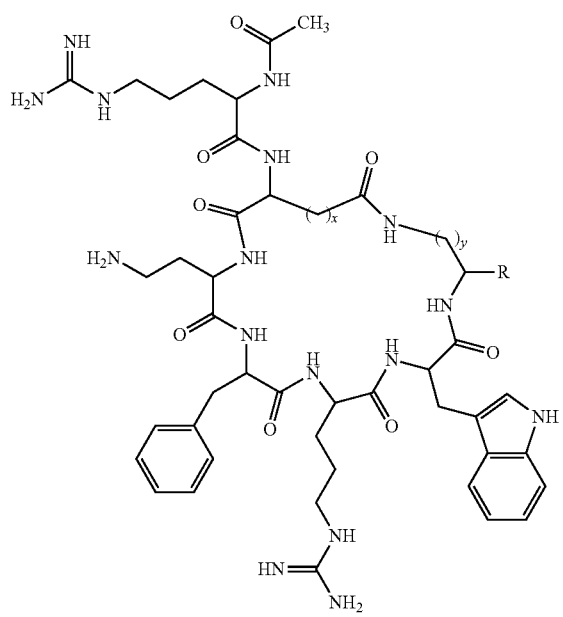

or a pharmaceutically acceptable salt thereof,
wherein:
R is —C(=O)—OH or —C(=O)—NH$_2$;
x is 1 or 2; and
y is 3 or 4.

The cyclic peptide may be one of formula (II):

(II)

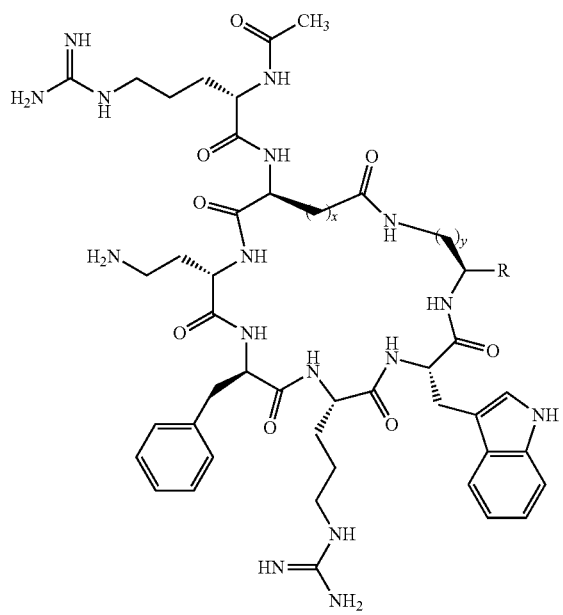

Thus the cyclic peptide may be

```
                                         (SEQ ID NO: 4)
Ac-Arg-cyclo(Asp-Dab-D-Phe-Arg-Trp-Lys)-NH2, (SEQ ID NO: 5)
Ac-Arg-cyclo(Asp-Dab-D-Phe-Arg-Trp-Lys)-OH, (SEQ ID NO: 6)
Ac-Arg-cyclo(Glu-Dab-D-Phe-Arg-Trp-Orn)-NH2
or (SEQ ID NO: 7)
Ac-Arg-cyclo(Glu-Dab-D-Phe-Arg-Trp-Orn)-OH.
```

In another aspect, the present invention provides a pharmaceutical composition comprising a cyclic peptide or pharmaceutically acceptable salt thereof of the invention and a pharmaceutically acceptable carrier.

In another aspect, the present invention provides a melanocortin receptor-specific peptide-based pharmaceutical composition for use in treatment of melanocortin receptor-mediated diseases, indications, conditions and syndromes.

In another aspect, the present invention provides a peptide-based melanocortin receptor-specific pharmaceutical, wherein the peptide is a selective MC4-R ligand, for use in treatment of sexual dysfunction and other MC4-R associated disorders.

In another aspect, the present invention provides peptides which are specific for MC4-R and which are agonists.

In another aspect, the present invention provides a melanocortin receptor-specific pharmaceutical for use in treatment sexual dysfunction without substantial adverse cardiovascular effects, including without a substantial increase in blood pressure.

In another aspect, the present invention provides a specific MC4-R cyclic peptide that is effective over a significant dose range.

Other aspects and novel features, and the further scope of applicability of the present invention will be set forth in part in the detailed description to follow, taken in conjunction with the accompanying drawings, and in part will become apparent to those skilled in the art upon examination of the following, or may be learned by practice of the invention. The aspects of the invention may be realized and attained by means of the instrumentalities and combinations particularly pointed out in the appended claims.

BRIEF DESCRIPTION OF THE DRAWINGS

The accompanying drawings, which are incorporated into and forms a part of the specification, illustrate one or more embodiments of the present invention and, together with the description, serves to explain the principles of the invention. The drawings are only for the purpose of illustrating one or more preferred embodiments of the invention and are not to be construed as limiting the invention.

DETAILED DESCRIPTION OF THE INVENTION

1.0 Definitions

Figure 1:
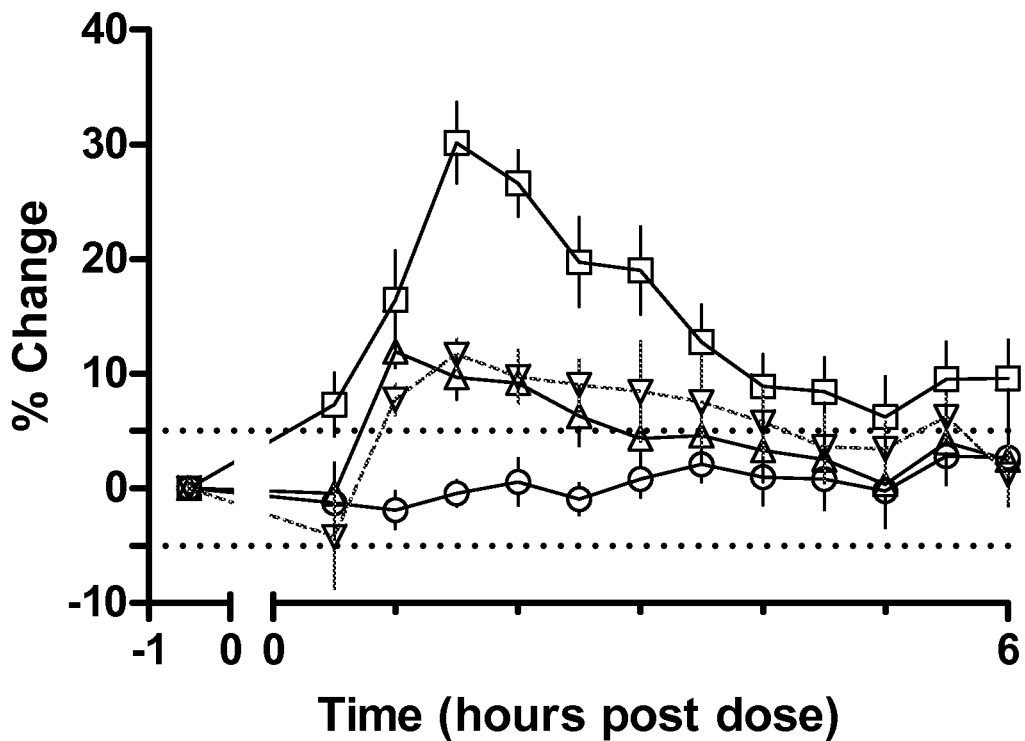
FIG. 1 is a plot of systolic blood pressure determined in a crossover study using surgically implanted pressure transducers monitored by telemetry, following administration of vehicle (○), bremelanotide at a dose of 1 μmol/kg by IV injection (□) and the cyclic peptide of Example 8.1 at doses of 0.84 μmol/kg (∇) and 3.0 μmol/kg (Δ) by subcutaneous injection.

Before proceeding with the description of the invention, certain terms are defined as set forth herein.

In the sequences given for the peptides according to the present invention, the amino acid residues have their conventional meaning as given in Chapter 2400 of the *Manual of Patent Examining Procedure*, 8th Ed., published by the United States Patent and Trademark Office. Thus, "Nle" is norleucine, "Asp" is aspartic acid, "His" is histidine, "Phe" is phenylalanine, "Arg" is arginine, "Trp" is tryptophan, and "Lys" is lysine, and so on. It is to be understood that "D" isomers are designated by a "D-" before the three letter code or amino acid name, such that for example D-Phe is D-phenylalanine. Amino acid residues not encompassed by the foregoing have the following definitions:

| Abbreviation | Common Name | Side Chain Structure |
|---|---|---|
| Dab | 2,4-diaminobutyric acid |  |
| Orn | ornithine | 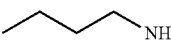 |

The term "Ac" means the acetyl group $CH_3\text{---}C(\!\!=\!\!O)\text{---}$.

An "amide" includes compounds that have a trivalent nitrogen attached to a carbonyl group ($\text{---}C(\!\!=\!\!O)\text{---}NH_2$), such as for example methylamide, ethylamide, propylamide, and the like.

An "amine" includes compounds that contain an amino group ($\text{---}NH_2$).

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

By a melanocortin receptor "agonist" is meant an endogenous substance, drug substance or compound, including a compound such as the peptides of the present invention, which can interact with a melanocortin receptor and initiate a pharmacological response, including but not limited to adenyl cyclase activation, characteristic of the melanocortin receptor. For the present invention, a melanocortin receptor agonist which is an agonist at melanocortin-4 receptor (MC4-R) is preferred, but for certain applications, a melanocortin receptor agonist which is an agonist at both MC4-R and melanocortin-1 receptor (MC1-R) is preferred, and for other applications a melanocortin receptor agonist which is an agonist at one or more of MC1-R, melanocortin-3 receptor (MC3-R), MC4-R and melanocortin-5 receptor (MC5-R) is preferred.

By "α-MSH" is meant the peptide Ac-Ser-Tyr-Ser-Met-Glu-His-Phe-Arg-Trp-Gly-Lys-Pro-Val-NH$_2$ (SEQ ID NO:8) and analogs and homologs thereof, including without limitation NDP-α-MSH.

By "NDP-α-MSH" is meant the peptide Ac-Ser-Tyr-Ser-Nle-Glu-His-D-Phe-Arg-Trp-Gly-Lys-Pro-Val-NH$_2$ (SEQ ID NO:9) and analogs and homologs thereof.

By "$EC_{50}$" is meant the molar concentration of an agonist, including a partial agonist, which produced 50% of the maximum possible response for that agonist. By way of example, a test compound which, at a concentration of 72 nM, produces 50% of the maximum possible response for that compound as determined in a cAMP assay in an MC4-R cell expression system has an $EC_{50}$ of 72 nM. Unless otherwise specified, the molar concentration associated with an $EC_{50}$ determination is in nanomoles per liter (nM).

By "Ki (nM)" is meant the equilibrium inhibitor dissociation constant representing the molar concentration of a competing compound that binds to half the binding sites of a receptor at equilibrium in the absence of radioligand or other competitors. In general, the numeric value of the Ki is inversely correlated to the affinity of the compound for the receptor, such that if the Ki is low, the affinity is high. Ki may be determined using the equation of Cheng and Prusoff (Cheng Y., Prusoff W. H., Biochem. Pharmacol. 22: 3099-3108, 1973):

$$Ki = \frac{EC_{50}}{1 + \frac{[\text{ligand}]}{K_D}}$$

where "ligand" is the concentration of radioligand and $K_D$ is an inverse measure of receptor affinity for the radioligand which produces 50% receptor occupancy by the radioligand. Unless otherwise specified, the molar concentration associated with a Ki determination is in nM. Ki may be expressed in terms of specific receptors (e.g., MC1-R, MC3-R, MC4-R or MC5-R) and specific ligands (e.g., α-MSH or NDP-α-MSH).

By "inhibition" is meant the percent attenuation, or decrease in receptor binding, in a competitive inhibition assay compared to a known standard. Thus, by "inhibition at 1 μM (NDP-α-MSH)" is meant the percent decrease in binding of NDP-α-MSH by addition of a determined amount of the compound to be tested, such as 1 μM of a test compound, such as under the assay conditions hereafter described. By way of example, a test compound that does not inhibit binding of NDP-α-MSH has a 0% inhibition, and a test compound that completely inhibits binding of NDP-α-MSH has a 100% inhibition. Typically, as described hereafter, a radio assay is used for competitive inhibition testing, such as with $I^{125}$-labeled NDP-α-MSH, or a lanthanide chelate fluorescent assay, such as with Eu-NDP-α-MSH. However, other methods of testing competitive inhibition are known, including use of label or tag systems other than radioisotopes, and in general any method known in the art for testing competitive inhibition may be employed in this invention. It may thus be seen that "inhibition" is one measure to determine whether a test compound attenuates binding of α-MSH to melanocortin receptors.

By "binding affinity" is meant the ability of a compound or drug to bind to its biological target, expressed herein as Ki (nM).

By "intrinsic activity" is meant the maximal functional activity achievable by a compound in a specified melanocortin receptor expressing cell system, such as the maximal stimulation of adenylyl cyclase. The maximal stimulation achieved by α-MSH or NDP-α-MSH is designated as an intrinsic activity of 1.0 (or 100%) and a compound capable of stimulating half the maximal activity that of α-MSH or NDP- α-MSH is designated as having an intrinsic activity of 0.5 (or 50%). A compound of this invention that under assay conditions described herein has an intrinsic activity of 0.7 (70%) or higher is classified as an agonist, a compound with intrinsic activity between 0.1 (10%) and 0.7 (70%) is classified as a partial agonist, and a compound with intrinsic activity below 0.1 (10%) is classified as inactive or having no intrinsic activity. In one aspect, the cyclic peptides of the present invention may generally be characterized as a partial agonist at MC4-R with respect to α-MSH or NDP-α-MSH.

In general, "functional activity" is a measure of the signaling of a receptor, or measure of a change in receptor-associated signaling, such as a melanocortin receptor, and in particular MC4-R or hMC4-R, upon stimulation by a compound. Melanocortin receptors initiate signal transduction through activation of heterotrimeric G proteins. In one aspect, melanocortin receptors signal through $G\alpha_s$, which catalyzes production of cAMP by adenylyl cyclase. Thus determination of stimulation of adenylyl cyclase, such as determination of maximal stimulation of adenylyl cyclase, is one measure of functional activity, and is the primary measure exemplified herein. However, it is to be understood that alternative measures of functional activity may be employed in the practice of this invention, and are specifically contemplated and included within the scope of this invention. Thus, in one example intracellular free calcium may be measured, such as reported by and using the methods disclosed in Mountjoy K. G. et al., Melanocortin receptor-medicated mobilization of intracellular free calcium in HEK293 cells. Physiol Genomics 5:11-19, 2001, or Kassack M. U. et al., Functional screening of G protein-coupled receptors by measuring intracellular calcium with a fluorescence microplate reader. Biomol Screening 7:233-246, 2002. It is also possible to measure activation by measurement of the production of inositol triphosphate or diacylglycerol from phosphatidylinositol 4,5-biphosphate, such as by use of radioassays. Yet another measure of functional activity is receptor internalization, resulting from activation of regulatory pathways, such as using the methods disclosed in Nickolls S. A. et al., Functional selectivity of melanocortin 4 receptor peptide and nonpeptide agonists: evidence for ligand specific conformational states. J Pharm Exper Therapeutics 313:1281-1288, 2005. Yet another measure of functional activity is the exchange, and exchange rate, of nucleotides associated with activation of a G protein receptor, such as the exchange of GDP (guanosine diphosphate) for GTP (guanosine triphosphase) on the G protein α subunit, which may be measured by any number of means, including a radioassay using guanosine 5'-(γ-[$^{35}$S]thio)-triphosphate, as disclosed in Manning D. R., Measures of efficacy using G proteins as endpoints: differential engagement of G proteins through single receptors. Mol Pharmacol 62:451-452, 2002. Various gene-based assays have been developed for measuring activation of G-coupled proteins, such as those disclosed in Chen W. et al., A colorimetric assay from measuring activation of Gs- and Gq-coupled signaling pathways. Anal Biochem 226:349-354, 1995; Kent T. C. et al., Development of a generic dual-reporter gene assay for screening G-protein-coupled receptors. Biomol Screening, 5:437-446, 2005; or Kotarsky K. et al., Improved receptor gene assays used to identify ligands acting on orphan seven-transmembrane receptors. Pharmacology & Toxicology 93:249-258, 2003. The colorimetric assay of Chen et al. has been adapted for use in measuring melanocortin receptor activation, as disclosed in Hruby V. J. et al., Cyclic lactam α-melanocortin analogues of Ac-Nle$^4$-cyclo[Asp$^5$,D-Phe$^7$,Lys$^{10}$] α-melanocyte-stimulating hormone-(4-10)-NH$_2$ with bulky aromatic amino acids at position 7 shows high antagonist potency and selectivity at specific melanocortin receptors. J Med Chem 38:3454-3461, 1995. In general, functional activity may be measured by any method, including methods of determining activation and/or signaling of a G-coupled receptor, and further including methods which may be hereafter developed or reported. Each of the foregoing articles, and the methods disclosed therein, is incorporated here by reference as if set forth in full.

The terms "treat," "treating" and "treatment," as used herein, contemplate an action that occurs while a patient is suffering from the specified disease or disorder, which reduces the severity of the disease or disorder.

As used herein, the term "therapeutically effective amount" means the amount of a compound including a peptide of the invention that will elicit a biological or medical response in the mammal that is being treated by a medical doctor or other clinician.

As used herein, the term "prophylactically effective" or "preventive" means the amount of a compound including a peptide of the invention that will prevent or inhibit affliction or mitigate affliction of a mammal with a medical condition that a medical doctor or other clinician is trying to prevent, inhibit, or mitigate before a patient begins to suffer from the specified disease or disorder.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

2.0 Clinical Indications and Utility

The compositions and methods disclosed herein can be used for both medical applications and animal husbandry or veterinary applications. Typically, the methods are used in humans, but may also be used in other mammals. The term "patient" is intended to denote a mammalian individual, and is so used throughout the specification and in the claims. The primary applications of the present invention involve human patients, but the present invention may be applied to laboratory, farm, zoo, wildlife, pet, sport or other animals.

Peptides, compositions and methods of the present invention may be employed for the treatment of sexual dysfunction, including both male erectile dysfunction and female sexual dysfunction. In one particular embodiment, the peptides, compositions and methods of the present invention are used in male patients to increase erectile function, including but not limiting to increasing erectile function so as to permit vaginal intercourse. In another particular embodiment, the peptides, compositions and methods of the present invention are used to treat female sexual dysfunction, including but not limited to an increase in arousal success rate, desire success rate, levels of arousal and desire. For female sexual dysfunction, endpoints may, but need not, be determined by any of a number of validated instruments, including but not limited to the Female Sexual Distress Scale, Female Sexual Encounter Profile, Female Sexual Function Index, and Global Assessment Questionnaire. Patients treated for female sexual dysfunction may be premenopausal women or postmenopausal women.

3.0 Combination Therapy for Certain Indications

The peptides, compositions and methods of the present invention may be used for treatment of any of the foregoing diseases, indications, conditions or syndromes, or any disease, indication, condition or syndrome which is melanocortin receptor mediated, by administration in combination with one or more other pharmaceutically active compounds. Such combination administration may be by means of a single dosage form which includes both a peptide of the present invention and one more other pharmaceutically active compounds, such single dosage form including a tablet, capsule, spray, inhalation powder, injectable liquid or the like. Alternatively, combination administration may be by means of administration of two different dosage forms, with one dosage form containing a peptide of the present invention, and the other dosage form including another pharmaceutically active compound. In this instance, the dosage forms may be the same or different. Without meaning to limit combination therapies, the following exemplifies certain combination therapies which may be employed.

3.1 Combination Therapy for Sexual Dysfunction.

It is possible and contemplated to use cyclic peptides of the present invention in combination with other drugs or agents for treatment of sexual dysfunction. These other drugs and agents may include agents that induce erectile activity, including phosphodiesterase-5 (PDE-5) inhibitors, testosterone, prostaglandin and the like. In a preferred embodiment of the invention, cyclic peptides of the invention are used in combination with a therapeutically effective amount of a cyclic-GMP-specific phosphodiesterase inhibitor or an alpha-adrenergic receptor antagonist. The teachings and disclosure of U.S. Pat. No. 7,235,625 entitled "Multiple Agent Therapy for Sexual Dysfunction" are incorporated here by reference as if set forth in full.

The present invention thus provides methods of treating sexual dysfunction, the methods comprising the step of administering to the patient having or at risk of having sexual dysfunction a therapeutically effective amount of a cyclic peptide of the present invention in combination with a therapeutically effective amount of a second sexual dysfunction pharmaceutical agent. The cyclic peptide of the present invention may be administered simultaneously with, prior to or subsequent to administration with a therapeutically effective amount of a second sexual dysfunction pharmaceutical agent. Preferably the peptide of the present invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the peptide of the present invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the peptide of the present invention when desired or needed by the patient.

The present invention thus provides methods of treating sexual dysfunction, the methods comprising the step of administering to a patient having or at risk of having sexual dysfunction a therapeutically effective amount of a cyclic peptide of the present invention in combination with another compound that is useful in the treatment of sexual dysfunction. In a preferred embodiment of combination therapy the sexual dysfunction is female sexual dysfunction. In an especially preferred embodiment of combination therapy the sexual dysfunction is erectile dysfunction.

The present invention also provides pharmaceutical compositions that comprise a cyclic peptide of the present invention and a second compound useful for the treatment of sexual dysfunction. In an embodiment of the composition, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphine; oxytocin modulators; a-adrenergic antagonists; androgens; selective androgen receptor modulators (SARMs); buproprion; vasoactive intestinal peptide (VIP); neutral endopeptidase inhibitors (NEP); and neuropeptide Y receptor antagonists (NPY).

In an embodiment of the method and composition, the second sexual dysfunction pharmaceutical agent is testosterone.

In another embodiment of combination therapy, the second sexual dysfunction pharmaceutical agent is a type V phosphodiesterase (PDE-5) inhibitor. For example, the PDE-5 inhibitor may be Viagra®, a brand of sildenafil, Levitra®, a brand of monohydrochloride salt of vardenafil, or Clalis®, a brand of tadalafil. Other PDE-5 inhibitors are disclosed in U.S. Pat. No. 7,235,625, issued Jun. 22, 2007, and entitled "Multiple Agent Therapy for Sexual Dysfunction", incorporated here by reference.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolidin-1- yl-ethoxy)-phenyl]-5,6,7,8-tetrahydro-napththalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[-4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a cyclic peptide of the present invention may be used in combination with any known mechanical aids or devices.

The present invention also provides kits for the treatment of sexual dysfunction (including erectile dysfunction), the kits comprising: a first pharmaceutical composition including a cyclic peptide of the present invention; a second pharmaceutical composition comprising a second compound useful for the treatment of sexual dysfunction; and, a container for the first and second compositions.

4.0 Methods of Administration and Use

The method of administration and use varies depending upon the characteristic of specific peptides of the present invention, the disease, indication, condition or syndrome to be treated, and other factors known to those in the art. In general, any method of administration and use known in the art or hereafter developed may be employed with the peptides of the present invention. Without limiting the foregoing, the following methods of administration and use have specific application for the indicated indications.

Compositions including one or more peptides of the present invention may administered by subcutaneous injection. In one aspect, a cyclic peptide of the present invention is formulated for a deep intramuscular injection, such as in the gluteal or deltoid muscle, of a formulation with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another aspect a cyclic peptide of the present invention is formulated with a poly(ortho ester), which may be an auto-catalyzed poly(ortho ester) with any of a variable percentage of lactic acid in the polymeric backbone, and optionally one or more additional excipients. In one aspect poly (D,L-lactide-co-glycolide) polymer is employed. In general, any of a number of injectable and bioerodible polymers, which are preferably also adhesive polymers, may be employed in a sustained release injectable formulation. Alternatively other sustained release formulations may be employed, including formulations permitting subcutaneous injection, which other formulations may include one or more of nano/microspheres (such as compositions including PLGA polymers), liposomes, emulsions (such as water-in-oil emulsions), gels, insoluble salts or suspensions in oil The formulation may be such that an injection is required on a daily, weekly, monthly or other periodic basis, depending on the concentration and amount of cyclic peptide, the sustained release rate of the materials employed, and other factors known to those of skill in the art.

Compositions including one or more peptides of the present invention may be administered orally in an individual dosage form such as a tablet or capsule. In one aspect, the individual dosage form includes an enteric coating, and optionally one or more agents to increase uptake, decrease protease degradation, increase cellular permeability, and the like.

For sexual dysfunction, in a preferred aspect one or more peptides of the present invention are formulated such that it may be administered on demand, such as about less than one hour, less than two hours or less than about four hours prior to anticipated sexual activity. In one aspect the composition is formulated for subcutaneous injection. In another aspect, the composition is formulated for any of a variety of transdermal routes of administration, including buccal administration, nasal administration, inhalation administration and the like. In another aspect the composition is formulated for nasal administration, such as a by means of a metered spray device delivering a volume of from about 20 to about 200 µL of an aqueous composition including any of a variety of other agents, including permeability enhancing agents.

5.0 Methods of Making

In general, the peptides of the present invention may be synthesized by solid-phase synthesis and purified according to methods known in the art. Any of a number of well-known procedures utilizing a variety of resins and reagents may be used to prepare the peptides of the present invention.

The cyclic peptides of the present invention may be readily synthesized by known conventional procedures for the formation of a peptide linkage between amino acids. Such conventional procedures include, for example, any solution phase procedure permitting a condensation between the free alpha amino group of an amino acid or residue thereof having its carboxyl group and other reactive groups protected and the free primary carboxyl group of another amino acid or residue thereof having its amino group or other reactive groups protected. In a preferred conventional procedure, the cyclic peptides of the present invention may be synthesized by solid-phase synthesis and purified according to methods known in the art. Any of a number of well-known procedures utilizing a variety of resins and reagents may be used to prepare the peptides of the present invention.

The process for synthesizing the cyclic peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide. The resulting peptide is then cyclized to yield a cyclic peptide of the invention.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods. These methods are disclosed in numerous references, including Merrifield, R. B., Solid phase synthesis (Nobel lecture). Angew Chem 24:799-810 (1985) and Barany et al., *The Peptides, Analysis, Synthesis and Biology* Vol. 2, Gross, E. and Meienhofer, J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl (Z—Cl), p-nitrobenzyloxycarbonyl (X—NO$_2$), p-bromobenzyloxycarbonyl (Z—Br), p-biphenyl-isopropoxycarbonyl, 9-fluorenylmethoxycarbonyl (Fmoc) and p-methoxybenzyloxycarbonyl (Moz) and aliphatic urethane-type protecting groups, such as t-butyloxycarbonyl (Boc), diisopropylmethoxycarbonyl, isopropoxycarbonyl, and allyloxycarbonyl (Alloc). Fmoc are preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pbf and Pmc are preferred protecting groups for Arg.

The peptides of the invention described herein were prepared using solid phase synthesis, such as by means of a Symphony Multiplex Peptide Synthesizer (Rainin Instrument Company) automated peptide synthesizer, using programming modules as provided by the manufacturer and following the protocols set forth in the manufacturer's manual.

Solid phase synthesis is commenced from the C-terminal end of the peptide by coupling a protected alpha amino acid to a suitable resin. Such starting material is prepared by attaching an alpha amino-protected amino acid by an ester linkage to a p-benzyloxybenzyl alcohol (Wang) resin, a 2-chlorotrityl chloride resin or an oxime resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Typically, orthogonal protecting groups are used as appropriate. For example, the peptides of the invention contain multiple amino acids with an amino group-containing side chain. In one aspect, an Allyl-Alloc protection scheme is employed with the amino acids forming a lactam bridge through their side chains, and orthogonal protecting groups, cleavable under different reactive conditions, use for other amino acids with amino group-containing side chains. Thus, for example, Fmoc-Lys(Alloc)-OH, Fmoc-Orn(Alloc)-OH, Fmoc-Dap(Alloc)-OH, Fmoc-Dab(Alloc)-OH, Fmoc-Asp (OAII)-OH or Fmoc-Glu(OAII)-OH amino acids can be employed for the positions forming a lactam bridge upon cyclization, while other amino acids with amino group-containing side chains have a different and orthogonal protecting group, such as with Fmoc-Arg(Pbf)-OH, Fmoc-Lys(Pbf)-OH, Fmoc-Dab(Pbf)-OH or the like. Other protecting groups may be similarly employed; by way of example and not limitation, Mtt/OPp (4-methyltrityl/2-phenylisopropyl) can be employed with the side chains forming a lactam bridge upon cyclization, with orthogonal protecting groups being utilized for other positions that are not cleavable using conditions suitable for cleavage of Mtt/OPp.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Similarly, methods for modifying side chains of amino acids are well known to those skilled in the art of peptide synthesis. The choice of modifications made to reactive groups present on the peptide will be determined, in part, by the characteristics that are desired in the peptide.

In the peptides of the present invention, in one preferred embodiment the N-terminus group is modified by introduction of an N-acetyl group. In one aspect, a method is employed wherein after removal of the protecting group at the N-terminal, the resin-bound peptide is reacted with acetic anhydride in dichloromethane in the presence of an organic base, such as diisopropylethylamine. Other methods of N-terminus acetylation are known in the art, including solution phase acetylation, and may be employed.

The peptide can, in one embodiment, be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris (pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCl/HOBt). Coupling is conventionally initiated by use of a suitable base, such as N,N-diisopropylethylamine (DIPEA), sym-collidine or N-methylmorpholine (NMM).

The cyclized peptides can then be cleaved from solid phase, using any suitable reagent, such as ethylamine in DCM or various combinations of agents, such as trifluoroacetic acid (TFA), tri-isopropylsilane (TIS), dimethoxybenezene (DMB), water and the like. The resulting crude peptide is dried and remaining amino acid side chain protecting groups, if any, are cleaved using any suitable reagent, such as (TFA in the presence of water, TIS, 2-mercaptopethane (ME) and/or 1,2-ethanedithiol (EDT). The final product is precipitated by adding cold ether and collected by filtration. Final purification is by reverse phase high performance liquid chromatography (RP-HPLC), using a suitable column, such as a $C_{18}$ column, or other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

While synthesis has been described primarily with reference to solid phase Fmoc chemistry, it is to be understood that other chemistries and synthetic methods may be employed to make the cyclic peptides of the invention, such as by way of example and not limitation, methods employing Boc chemistry, solution chemistry, and other chemistries and synthetic methods.

6.0 Formulations

Depending on the desired route of administration, the formulation of a composition including one or more cyclic peptides of the present invention may be varied. Thus the formulation may be suitable for subcutaneous injection, or intravenous injection, for topical applications, for ocular applications, for nasal spray applications, for inhalation applications, for other transdermal applications and the like.

6.1 Salt Form of Cyclic Peptides of the Present Invention.

The cyclic peptides of the present invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the cyclic peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides of the present invention are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate, ammonium acetate and trifluoroacetic acid salt forms are especially useful. Where the peptides of the present invention include an acidic moiety, suitable pharmaceutically acceptable salts may include alkali metal salts, such as sodium or potassium salts, or alkaline earth metal salts, such as calcium or magnesium salts.

6.2 Pharmaceutical Compositions.

The invention provides a pharmaceutical composition that includes a cyclic peptide of the present invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The cyclic peptide compositions of the present invention may be formulated or compounded into pharmaceutical compositions that include at least one cyclic peptide of the present invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of the present invention over a period of time.

In general, the actual quantity of cyclic peptides of the present invention administered to a patient will vary between fairly wide ranges depending on the mode of administration, the formulation used, and the response desired.

In practical use, the cyclic peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, rectal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or non-aqueous techniques. The amount of active peptide in such therapeutically useful compositions is such that an effective dosage will be obtained. In another advantageous dosage unit form, sublingual constructs may be employed, such as sheets, wafers, tablets or the like.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Cyclic peptides may also be administered parenterally. Solutions or suspensions of these active peptides can be prepared in water suitably mixed with a surfactant such as hydroxypropylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The cyclic peptides of the present invention may be therapeutically applied by means of nasal administration. By "nasal administration" is meant any form of intranasal administration of any of the cyclic peptides of the present invention. The peptides may be in an aqueous solution, such as a solution including saline, citrate or other common excipients or preservatives. The peptides may also be in a dry or powder formulation.

The cyclic peptides of the present invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the cyclic peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

In an alternative embodiment, cyclic peptides of the present invention may be administered directly into the lung. Intrapulmonary administration may be performed by means of a metered dose inhaler, a device allowing self-administration of a metered bolus of a peptide of the present invention when actuated by a patient during inspiration. In one aspect of this embodiment, the cyclic peptide may be in a dried and particulate form, for example particles between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With microparticles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multi-dose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The cyclic peptides of the present invention may be therapeutically administered by means of an injection, typically a deep intramuscular injection, such as in the gluteal or deltoid muscle, of a time release injectable formulation. In one embodiment, a cyclic peptide of the present invention is formulated with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a cyclic peptide of the present invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer is employed. In general, any of a number of injectable and bioerodible polymers, which are preferably also adhesive polymers, may be employed in a time release injectable formulation. The formulation may be such that an injection is required on a weekly, monthly or other periodic basis, depending on the concentration and amount of cyclic peptide, the bioerosion rate of the polymer, and other factors known to those of skill in the art.

6.3 Oral Formulations of Peptides of the Present Invention.

In one aspect, the cyclic peptides of the present invention are formulated for oral delivery. The peptide is preferably formulated and made such that it is encased in an enteric protectant, more preferably such that it is not released until the tablet or capsule has transited the stomach, and optionally has further transited a portion of the small intestine. In the context of this application it will be understood that the term enteric coating or material refers to a coating or material that will pass through the stomach essentially intact but will rapidly disintegrate in the small intestine to release the active drug substance. One enteric coating solution that may be used includes cellulose acetate phthalate, and optionally other ingredients such as ammonium hydroxide, triacetin, ethyl alcohol, methylene blue, and purified water. Cellulose acetate phthalate is a polymer that has been used in the pharmaceutical industry for enterically coating individual dosage forms such as tablets and capsules, and is not soluble in water at a pH of less than about 5.8. Enteric coatings including cellulose acetate phthalate provide protection against the acidic environment of the stomach, but begin to dissolve in environment of the duodenum (pH of about 6-6.5), and are completely dissolved by the time the dosage form reaches the ileum (pH of about 7-8). In addition to cellulose acetate phthalate, other enteric coating materials are known and may be used with peptides of the present invention, including without limitation hydroxypropylmethylethylcellulose succinate, hydroxypropylmethylcellulose phthalate, polyvinyl acetate phthalate, and methacrylic acid-methyl methacrylate copolymer. The enteric coating employed promotes dissolution of the dosage form primarily at a site outside the stomach, and may be selected such that the enteric coating dissolves at a pH of approximately at least 6.0, more preferable at a pH of from about 6.0 to about 8.0. In one preferred aspect, the enteric coating dissolves and breaks down in the proximity of the ileum.

Any of a variety of permeation enhancers may be employed, to increase uptake in the intestines upon dissolution of the enteric coating. In one aspect, permeation enhancers increase either paracellular or transcellular transport systems. An increase in paracellular transport can be achieved by opening the tight junctions of the cells; an increase in transcellular transport can be achieved by increasing the fluidity of the cell membrane. Representative, non-limiting examples of such permeation enhancers include calcium chelators, bile salts (such as sodium cholate), and fatty acids. The peptides of the present invention may be in an enteric-coated individual dosage form that includes a fatty acid, such as for example oleate, palmitate, stearate, sodium caprate, or conjugated linoleic acid, in an enteric-coated capsule, to increase paracellular transport.

In one aspect, the individual dosage form, such as a tablet or capsule, optionally further includes common pharmaceutical binders such as povidone, diluents, glidants, fillers such as microcrystalline cellulose, lubricants such as magnesium stearate, disintegrants such as croscarmellose sodium, preservatives, colorants and the like in their usual known sizes and amounts. In some embodiments, peptides or polypeptides that act as substrates for intestinal proteases are further added.

6.4 Routes of Administration.

If a composition including one or more cyclic peptides of the present invention is administered by injection, the injection may be intravenous, subcutaneous, intramuscular, intraperitoneal or other means known in the art. The peptides of the present invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, rectal administration and the like.

6.5 Therapeutically Effective Amount.

In general, the actual quantity of cyclic peptide of the present invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition of the present invention that is sufficient to therapeutically alleviate sexual dysfunction in a patient, or to prevent or delay onset or recurrence of the sexual dysfunction.

In general, the cyclic peptides of the present invention are highly active. For example, the cyclic peptide can be administered at about 0.1, 0.5, 1, 5, 50, 100, 500, 1000 or 5000 µg/kg body weight, depending on the specific peptide selected, the desired therapeutic response, the route of administration, the formulation and other factors known to those of skill in the art.

7.0 Tests and Assays Employed in Evaluation of the Peptides of the Present Invention The melanocortin receptor-specific cyclic peptides of the present invention of this invention may be tested by a variety of assay systems and animal models to determine binding, functional status and efficacy.

7.1 Competitive Inhibition Assay Using $[I^{125}]$-NDP-α-MSH.

A competitive inhibition binding assay is performed using membrane homogenates prepared from HEK-293 cells that express recombinant hMC4-R, hMC3-R, or hMC5-R, and from B-16 mouse melanoma cells (containing endogenous MC1-R). In some instances, HEK-293 cells that express recombinant hMC1-R were employed. In the examples that follow, all MC3-R, MC4-R and MC5-R values are for human recombinant receptors. MC1-R values are for B-16 mouse melanoma cells, unless the heading is "hMC1-R", in which case the value is for human recombinant MC1-R. Assays were performed in 96 well GF/B Millipore multiscreen filtration plates (MAFB NOB10) pre-coated with 0.5% bovine serum albumin (Fraction V). Membrane homogenates were incubated with 0.2 nM (for hMC4-R) 0.4 nM (for MC3-R and MC5-R) or 0.1 nM (for mouse B16 MC1-R or hMC1-R) $[I^{125}]$-NDP-α-MSH (Perkin Elmer) and increasing concentrations of cyclic peptides of the present invention in buffer containing 25 mM HEPES buffer (pH 7.5) with 100 mM NaCl, 2 mM $CaCl_2$, 2 mM $MgCl_2$, 0.3 mM 1,10-phenanthroline, and 0.2% bovine serum albumin. After incubation for 60 minutes at 37° C., the assay mixture was filtered and the membranes washed three times with ice-cold buffer. Filters were dried and counted in a gamma counter for bound radioactivity. Non-specific binding was measured by inhibition of binding of $[I^{125}]$-NDP-α-MSH in the presence of 1 µM NDP-α-MSH. Maximal specific binding (100%) was defined as the difference in radioactivity (cpm) bound to cell membranes in the absence and presence of 1 µM NDP-α-MSH. Radioactivity (cpm) obtained in the presence of test compounds was normalized with respect to 100% specific binding to determine the percent inhibition of $[I^{125}]$-NDP-α-MSH binding. Each assay was conducted in triplicate and the actual mean values are described, with results less than 0% reported as 0%. Ki values for cyclic peptides of the present invention were determined using Graph-Pad Prism® curve-fitting software. Reported data herein for binding to hMC1-R and hMC4-R utilized $[I^{125}]$-NDP-α-MSH, as did some data with hMC3-R.

7.2 Competitive Binding Assay Using Eu-NDP-α-MSH

Alternatively, a competitive inhibition binding assay was performed employing Eu-NDP-α-MSH (PerkinElmer Life Sciences catalog No. AD0225) with determination by time-resolved fluorometry (TRF) of the lanthanide chelate. In comparison studies with $[I^{125}]$-NDP-α-MSH, the same values, within experimental error ranges, were obtained for percent inhibition and Ki. Typically competition experiments to determine Ki values were conducted by incubating membrane homogenates prepared from HEK-293 cells that express recombinant hMC4-R with 9 different concentrations of cyclic peptides of the present invention and 1 nM of Eu- NDP-α-MSH in a solution containing 25 mM HEPES buffer with 100 mM NaCl, 2 mM CaCl$_2$, 2 mM MgCl$_2$, 0.1% BSA, and 0.3 mM 1,10-phenanthroline. After incubation for 90 minutes at 37° C., the reaction was stopped by filtration over AcroWell 96-well filter plates (Pall Life Sciences). The filter plates were washed 4 times with 200 µL of ice-cold phosphate-buffered saline. DELFIA Enhancement solution (PerkinElmer Life Sciences) was added to each well. The plates were incubated on a shaker for 15 minutes and read at 340 nm excitation and 615 nm emission wavelengths. Each assay was conducted in duplicate and mean values were utilized. Ki values were determined by curve-fitting with Graph-Pad Prism® software using a one-site fixed-slope competition binding model. Reported data herein for binding to hMC5-R and some data with hMC3-R utilized hMC4-R utilized Eu-NDP-α-MSH.

7.3 Competitive Binding Assay using [I$^{125}$]-AgRP (83-132).

Competitive binding studies using [I$^{125}$]-AgRP (83-132) are carried out using membrane homogenates isolated from cells that express hMC4-R. The assays were performed in 96-well GF/B Millipore multiscreen filtration plates (MAFB NOB10) pre-coated with 0.5% bovine serum albumin (Fraction V). The assay mixture contained 25 mM HEPES buffer (pH 7.5) with 100 mM NaCl, 2 mM CaCl$_2$, 2 mM MgCl$_2$, 0.3 mM 1,10-phenanthroline, 0.5% bovine serum albumin, membrane homogenates, radioligand [I$^{125}$]-AgRP (83-132) (Perkin Elmer) and increasing concentrations of peptides of the present invention in a total volume of 200 µL. Binding was measured at radioligand concentrations of 0.2 nM. After incubating for 1 hour at 37° C., the reaction mixture was filtered and washed with assay buffer containing 500 mM NaCl. The dried discs were punched out from the plate and counted on a gamma counter. The total binding of the radioligand did not exceed 10% of the counts added to the reaction mixture. Ki values for cyclic peptides of the present invention were determined using Graph-Pad Prism® curve-fitting software.

7.4 Assay for Agonist Activity.

Accumulation of intracellular cAMP is examined as a measure of the ability of the cyclic peptides of the present invention to elicit a functional response in HEK-293 cells that express MC4-R. Confluent HEK-293 cells that express recombinant hMC4-R were detached from culture plates by incubation in enzyme-free cell dissociation buffer. Dispersed cells were suspended in Earle's Balanced Salt Solution containing 10 mM HEPES (pH 7.5), 1 mM MgCl$_2$, 1 mM glutamine, 0.5% albumin and 0.3 mM 3-isobutyl-1-methyl-xanthine (IBMX), a phosphodiesterase inhibitor. The cells were plated in 96-well plates at a density of 0.5×10$^5$ cells per well and pre-incubated for 30 minutes. Cells were exposed for 1 hour at 37° C. to test cyclic peptides of the present invention dissolved in DMSO (final DMSO concentration of 1%) at a concentration range of 0.05-5000 nM in a total assay volume of 200 µL. NDP-α-MSH was used as the reference agonist. At the end of the incubation period, cells were disrupted by the addition of 50 µL of lysis buffer (cAMP EIA kit, Amersham) followed by vigorous pipetting. Levels of cAMP in the lysates were determined using a cAMP EIA kit (Amersham). Data analysis was performed by nonlinear regression analysis with Graph-Pad Prism® software. The maximum efficacies of the cyclic peptides of the present invention were compared to that achieved by the reference melanocortin agonist NDP-αMSH.

7.5 Food Intake and Body Weight Change.

Change in food intake and body weight is evaluated for selected peptides administered by intravenous (IV) or subcutaneous injection routes. Male Sprague-Dawley rats are obtained from Hilltop Lab Animals, Inc. (Scottsdale, Pa.) or other vendors. Animals are individually housed in conventional polystyrene hanging cages and maintained on a controlled 12 hour on/off light cycle. Water and pelleted food is provided ad libitum. The rats are dosed IV with vehicle or selected peptides (0.3 to 1.0 mg/kg), or dosed subcutaneously with vehicle or selected peptides (doses up to 30 mg/kg). The changes in body weight and food intake for the 24 hour period after dosing are determined. The changes in body weight and food intake for the 48 hour and 72 hour periods after dosing are also measured to determine reversal of changes in body weight and food intake effects back to baseline levels.

7.6 Induction of Penile Erection.

The ability of peptides of the present invention to induce penile erection (PE) in male rats are evaluated with selected peptides. Male Sprague-Dawley rats weighing 250-300 g are kept on a 12 hour on/off light cycle with food and water ad libitum. All behavioral studies are performed between 9 a.m. and 4 p.m. Groups of 6-8 rats are administered peptides at a variety of doses via an IV route. Immediately after treatment, rats are placed into individual polystyrene cages (27 cm long, 16 cm wide, and 25 cm high) for behavioral observation, typically by remote video monitoring. Rats are observed for one hour, and the number of yawns, grooming bouts and PEs are recorded in 10-minute bins.

8.0 Peptides of the Invention

The cyclic peptides encompassed within formula (I) contain one or more asymmetric elements such as stereogenic centers, stereogenic axes and the like, so that the peptides encompassed within formula (I) can exist in different stereoisomeric forms. For both specific and generically described peptides, including the peptides encompassed within formula (I), all forms of isomers at all chiral or other isomeric centers, including enantiomers and diastereomers, are intended to be covered herein. The peptides of the invention each include multiple chiral centers, and may be used as a racemic mixture or an enantiomerically enriched mixture, in addition to use of the peptides of the invention in enantiopure preparations. Typically, the peptides of the invention will be synthesized with the use of chirally pure reagents, such as specified L- or D-amino acids, using reagents, conditions and methods such that enantiomeric purity is maintained, but it is possible and contemplated that racemic mixtures may be made. Such racemic mixtures may optionally be separated using well-known techniques and an individual enantiomer may be used alone. In cases and under specific conditions of temperature, solvents and pH wherein peptides may exist in tautomeric forms, each tautomeric form is contemplated as being included within this invention whether existing in equilibrium or predominantly in one form. Thus a single enantiomer of a peptide of formula (I), which is an optically active form, can be obtained by asymmetric synthesis, synthesis from optically pure precursors, or by resolution of the racemates.

The peptides of formula (II) are specific stereoisomeric forms of the peptides of formula (I), but the invention should not be construed as being limited to the stereoisomeric forms encompassed by formula (II).

The invention is further intended to include prodrugs of the present peptides, which on administration undergo chemical conversion by metabolic processes before becoming active pharmacological peptides. In general, such prodrugs will be functional derivatives of the present peptides, which are readily convertible in vivo into a peptide of formula (I). Prodrugs are any covalently bonded compounds, which release the active parent peptide drug of formula (I) in vivo. Conventional procedures for the selection and preparation of suitable prodrug derivatives are described, for example, in "Design of Prodrugs", ed. H. Bundgaard, Elsevier, 1985. Typical examples of prodrugs have biologically labile protecting groups on a functional moiety, such as for example by esterification of hydroxyl, carboxyl or amino functions. Thus by way of example and not limitation, a prodrug includes peptides of formula (I) wherein an ester prodrug form is employed, such as, for example, lower alkyl esters of the R group of formula (I), such as where R is —OH, which lower alkyl esters may include from 1-8 carbons in an alkyl radical or aralkyl esters which have 6-12 carbons in an aralkyl radical. Broadly speaking, prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce an active parent peptide drug of formula (I) in vivo.

The subject invention also includes peptides which are identical to those recited in formula (I), but for the fact that one or more atoms depicted in formula (I) are replaced by an atom having an atomic mass or mass number different from the atomic mass or mass number usually found in nature. Examples of isotopes that can be incorporated into compounds of the invention include isotopes of hydrogen, carbon, nitrogen and oxygen, such as $^2H$, $^3H$, $^{13}C$, $^{14}C$, $^{15}N$, $^{18}O$ and $^{17}O$, respectively. Peptides of the present invention and pharmaceutically acceptable salts or solvates of said compounds which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, may have use in a variety of assays, such as drug and/or substrate tissue distribution assays. Substitution with heavier isotopes, such as substitution of one or more hydrogen atoms with deuterium ($^2H$), can provide pharmacological advantages in some instances, including increased metabolic stability. Isotopically labeled peptides of formula (I) can generally be prepared by substituting an isotopically labeled reagent for a non-isotopically labeled reagent.

8.1 The Peptide of the Following Structure was Synthesized:

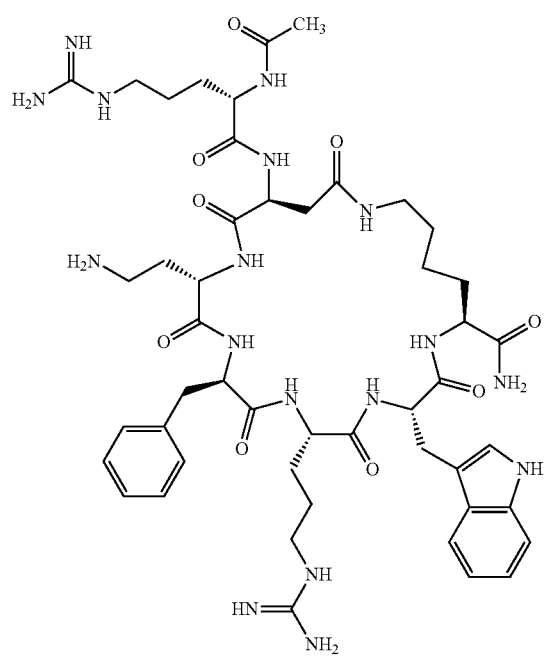 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O]

This peptide has the amino acid sequence Ac-Arg-cyclo(Asp-Dab-D-Phe-Arg-Trp-Lys)-NH$_2$. The cyclic peptide of Example 8.1 was prepared as the acetate (AcOH) and trifluoroacetic acid (TFA) salt forms. The cyclic peptide of Example 8.1 has the molecular formula $C_{48}H_{71}N_{17}O_9$, and has a calculated molecular weight of 1030.19. The molecular weight of the cyclic peptide of Example 8.1 as the acetate salt form was 1210.34, and as the TFA salt form was 1372.25.

The cyclic peptide of Example 8.1 was evaluated for binding against MC1-R, MC3-R, MC4-R and MC5-R in competitive studies using NDP-α-MSH, and was found to be selective for MC4-R, with a Ki value of 4.0 nM at MC4-R (average of four studies), a Ki value of 9 nM for MC1-R (average of five studies), a Ki value of 150 nM for MC3-R (average of two studies) and a Ki value of 2270 nM for MC5-R (average of two studies). In functional studies, the cyclic peptide of Example 8.1 was determined to be an agonist at MC4-R, with intrinsic activity of 91% at MC4-R where NDP-α-MSH is 100%, and with an EC$_{50}$ of 0.3 nM (average of five studies).

In rat penile erection studies, using bremelanotide (a non-specific MC4-R agonist of the formula Ac-Nle-cyclo(Asp-His-D-Phe-Arg-Trp-Lys)-OH)) as a positive control, the cyclic peptide of Example 8.1 was found to result in a statistically significant increase in observed spontaneous erections in a rat model compared to vehicle controls. Vehicle alone administered by a subcutaneous route resulted in an average of 0.429±0.202 spontaneous erections per rat in one hour (n=7), while subcutaneously administered cyclic peptide of Example 8.1 at a dose of 0.3 mg/kg resulted in an average of 2.286±0.286 spontaneous erections per rat in one hour (n=7) and at a dose of 1.0 mg/kg resulted in an average of 4.571±1.088 spontaneous erections per rat in one hour (n=7). The positive control, bremelanotide administered IV at a dose of 1 mg/kg, resulted in an average of 4±0.535 spontaneous erections per rat in one hour (n=7).

Surprisingly and advantageously, it was found in rat models of systolic blood pressure, using surgically implanted pressure transducers monitored by telemetry, that the cyclic peptide of Example 8.1 resulted in less increase of systolic blood pressure than did a dose of bremelanotide producing comparable results in penile erection studies. FIG. 1 shows the results in crossover studies using 8 transducer-implanted animals receiving the cyclic peptide of Example 8.1 at doses of 0.84 μmol/kg and 3.0 μmol/kg by subcutaneous injection and bremelanotide at a dose of 1 μmol/kg by IV injection, where in companion studies penile erections per rat per hour of the same doses and routes of administration showed the same or higher penile erection results with the cyclic peptide of Example 8.1 at 3.0 μmol/kg than with bremelanotide at 1 μmol/kg. In other studies, including comparisons of the same quantities of the cyclic peptide of Example 8.1 and bremelanotide by the same routes of administration, substantially similar results were obtained.

8.2 The Peptide of the Following Structure was Synthesized:

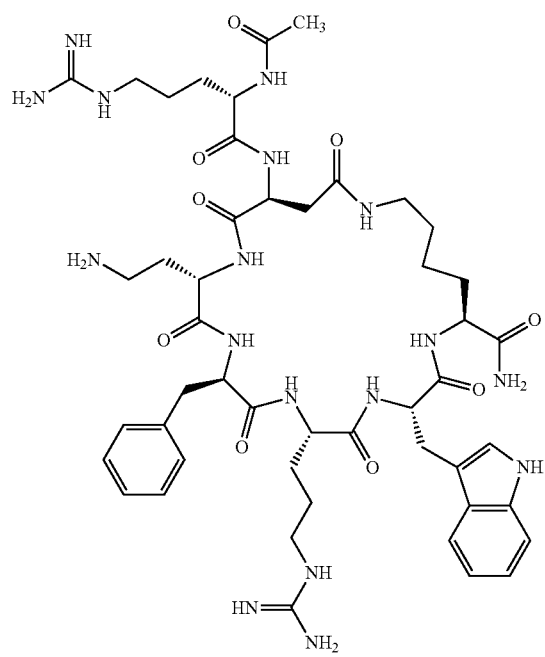 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O]

This peptide has the amino acid sequence Ac-Arg-cyclo(Asp-Dab-D-Phe-Arg-Trp-Lys)-OH. The cyclic peptide of Example 8.2 was prepared as the TFA salt form. The cyclic peptide of Example 8.2 has the molecular formula $C_{48}H_{70}N_{16}O_{10}$, and has a calculated molecular weight of 1031.17. The molecular weight of the cyclic peptide of Example 8.2 as the TFA salt form was 1373.23.

The cyclic peptide of Example 8.2 was evaluated for binding against MC1-R, MC3-R, MC4-R and MC5-R in competitive studies using NDP-α-MSH, and was found to be selective for MC4-R, with a Ki value of 57 nM at MC4-R (average of two studies), a Ki value of 234 nM for MC1-R (average of three studies), a Ki value of 5804 nM for MC3-R (average of two studies) and a Ki value over 10,000 nM for MC5-R (average of two studies). In functional studies, the cyclic peptide of Example 8.1 was determined to be an agonist at MC4-R, with intrinsic activity of 91% at MC4-R where NDP-α-MSH is 100%, and with an $EC_{50}$ of 4 nM (average of four studies).

8.3 The Peptide of the Following Structure was Synthesized:

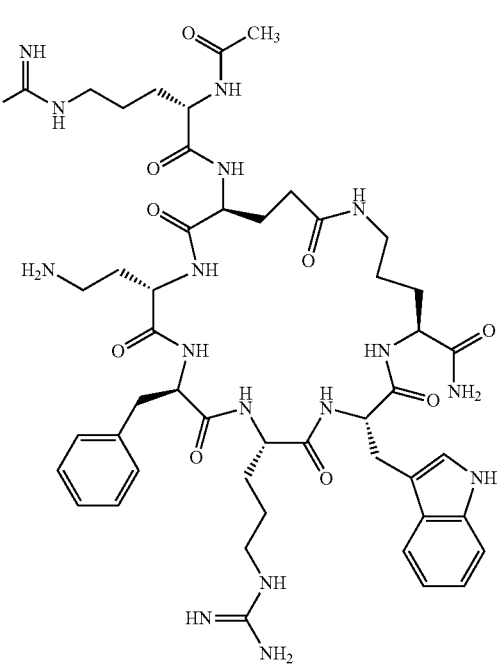

This peptide has the amino acid sequence Ac-Arg-cyclo(Glu-Dab-D-Phe-Arg-Trp-Orn)-NH$_2$. The cyclic peptide of Example 8.3 was prepared as the TFA salt form. The cyclic peptide of Example 8.3 has the molecular formula $C_{48}H_{71}N_{17}O_{9}$, and has a calculated molecular weight of 1030.19. The molecular weight of the cyclic peptide of Example 8.3 as the TFA salt form was 1372.25.

The cyclic peptide of Example 8.3 was evaluated for binding against MC1-R, MC3-R, MC4-R and MC5-R in competitive studies using NDP-α-MSH, and was found to have a Ki value of 0.65 nM at MC4-R (average of two studies), a Ki value of 1 nM for MC1-R (average of three studies), a Ki value of 74 nM for MC3-R (average of two studies) and a Ki value of 300 nM for MC5-R (average of two studies). In functional studies, the cyclic peptide of Example 8.3 was determined to be an agonist at MC4-R, with intrinsic activity of 94% at MC4-R where NDP-α-MSH is 100%, and with an $EC_{50}$ of 0.3 nM (average of five studies).

8.4 The Peptide of the Following Structure was Synthesized:

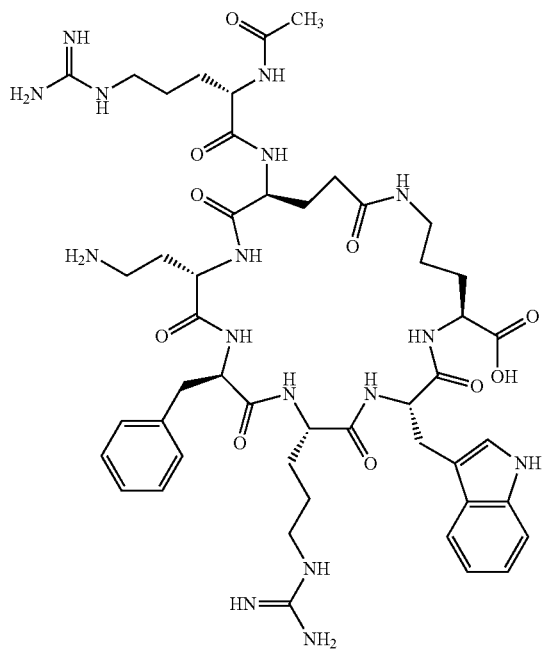 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2)NC(=O)[C@H](CCN)NC1=O]

This peptide has the amino acid sequence Ac-Arg-cyclo(Glu-Dab-D-Phe-Arg-Trp-Orn)-OH. The cyclic peptide of Example 8.4 was prepared as the acetate and TFA salt forms. The cyclic peptide of Example 8.4 has the molecular formula $C_{48}H_{70}N_{16}O_{10}$, and has a calculated molecular weight of 1031.17. The molecular weight of the cyclic peptide of Example 8.4 as the acetate salt form was 1211.32, and as the TFA salt form was 1373.23.

The cyclic peptide of Example 8.4 was evaluated for binding against MC1-R, MC3-R, MC4-R and MC5-R in competitive studies using NDP-α-MSH, and was found to have a Ki value of 8 nM at MC4-R (average of two studies), a Ki value of 4 nM for MC1-R (one study), a Ki value of 410 nM for MC3-R (one study) and a Ki value of 2366 nM for MC5-R (average of two studies). In functional studies, the cyclic peptide of Example 8.4 was determined to be an agonist at MC4-R, with intrinsic activity of 91% at MC4-R where NDP-α-MSH is 100%, and with an $EC_{50}$ of 3 nM (average of nine studies).

In rat penile erection studies, using bremelanotide as a positive control, the cyclic peptide of Example 8.4 was found to result in a statistically significant increase in observed spontaneous erections in a rat model compared to vehicle controls. Vehicle alone administered by a subcutaneous route resulted in an average of 0.429±0.202 spontaneous erections per rat in one hour (n=7), while subcutaneously administered cyclic peptide of Example 8.4 at a dose of 0.3 mg/kg resulted in an average of 2.571±0.685 spontaneous erections per rat in one hour (n=7) and at a dose of 1.0 mg/kg resulted in an average of 5.286±0.918 spontaneous erections per rat in one hour (n=7). The positive control, bremelanotide administered IV at a dose of 1 mg/kg, resulted in an average of 4±0.535 spontaneous erections per rat in one hour (n=7).

Figure 2:
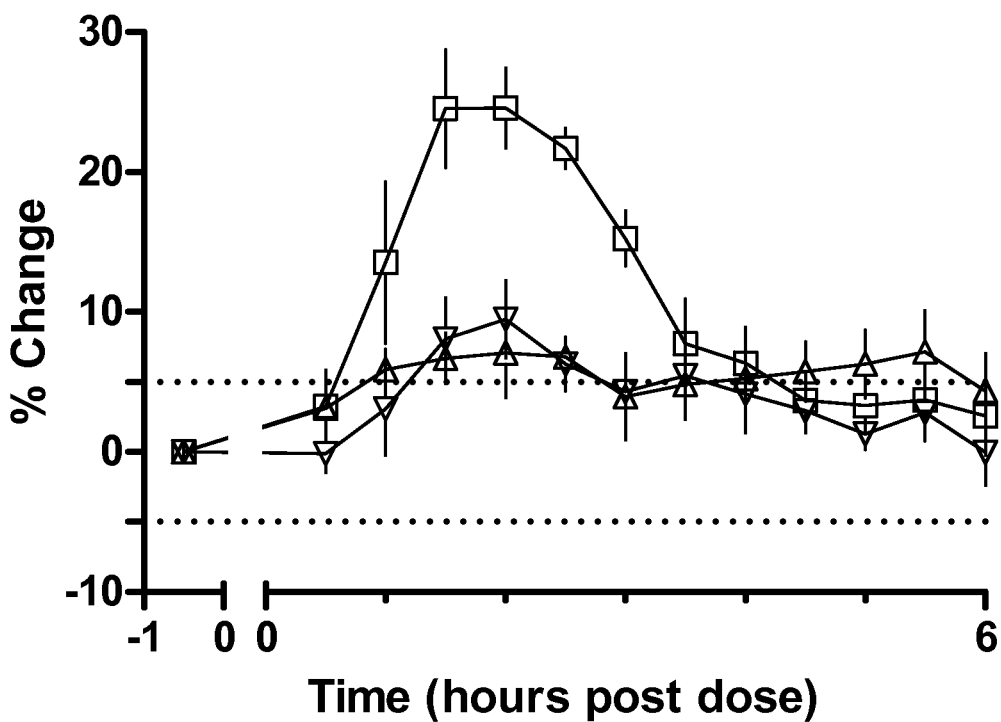
FIG. 2 is a plot of systolic blood pressure determined in a crossover study using surgically implanted pressure transducers monitored by telemetry, following administration of two different lots of the cyclic peptide of Example 8.4 at doses of 1 mg/kg by subcutaneous injection (∇, Δ) and bremelanotide at a dose of 1 mg/kg by IV injection (□).

Surprisingly and advantageously, it was found in rat models of systolic blood pressure, using surgically implanted pressure transducers monitored by telemetry, that the cyclic peptide of Example 8.4 resulted in less increase of systolic blood pressure than did a dose of bremelanotide producing comparable results in penile erection studies. FIG. 2 shows the results in crossover studies using 8 transducer-implanted animals receiving the cyclic peptide of Example 8.4 at doses of 1 mg/kg by subcutaneous injection and bremelanotide at a dose of 1 mg/kg by IV injection, where in companion studies penile erections per rat per hour of the same doses and routes of administration showed the same or higher penile erection results with the cyclic peptide of Example 8.4 at 1 mg/kg than with bremelanotide at 1 mg/kg. In other studies, including comparisons of the same quantities of the cyclic peptide of Example 8.4 and bremelanotide by the same routes of administration, substantially similar results were obtained.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

What is claimed is:

1. A method for treating female sexual dysfunction, comprising the step of administering a pharmaceutical composition comprising a pharmaceutically acceptable carrier and a cyclic peptide of formula (I):

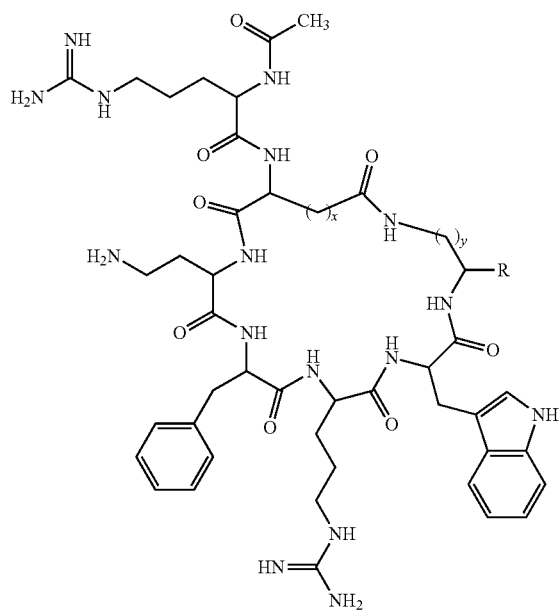

including all enantiomers, stereoisomers or diastereoisomers thereof, or a pharmaceutically acceptable salt of any of the foregoing,
wherein:
R is —C(=O)—OH or —C(=O)—NH₂;
x is 1 or 2; and
y is 3 or 4.

2. The method of claim 1 wherein the cyclic peptide is of formula (II):

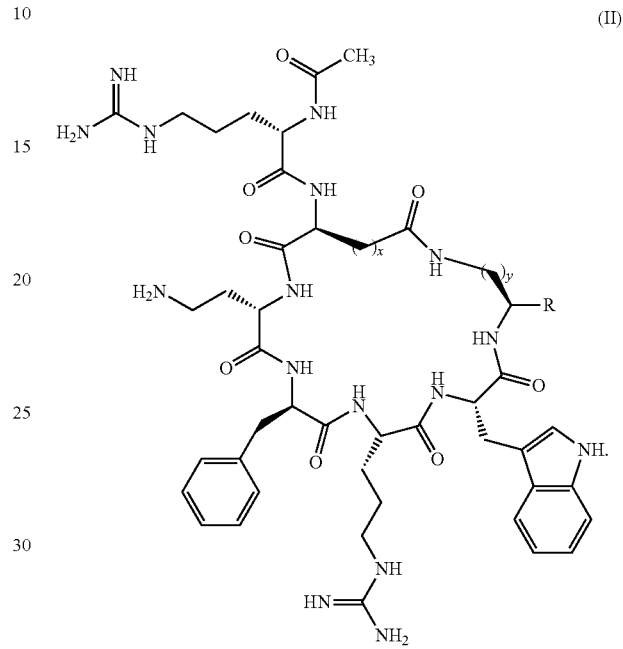

3. The method of claim 1 wherein the cyclic peptide is Ac-Arg-cyclo(Asp-Dab-D-Phe-Arg-Trp-Lys)-NH₂ (SEQ ID NO:4).

4. The method of claim 1 wherein the cyclic peptide is Ac-Arg-cyclo(Asp-Dab-D-Phe-Arg-Trp-Lys)-OH (SEQ ID NO:5).

5. The method of claim 1 wherein the cyclic peptide is Ac-Arg-cyclo(Glu-Dab-D-Phe-Arg-Trp-Orn)-NH₂ (SEQ ID NO:6).

6. The method of claim 1 wherein the cyclic peptide is Ac-Arg-cyclo(Glu-Dab-D-Phe-Arg-Trp-Orn)-OH (SEQ ID NO:7)

7. The method of claim 1 wherein the step of administering comprises oral, parenteral, urethral, vaginal, rectal, nasal, buccal, or sublingual administration.

8. The method of claim 1, wherein the step of administering comprises subcutaneous administration.

9. The method of claim 1, further comprising the step of administration of a second sexual dysfunction pharmaceutical agent.

* * * * *